United States Patent [19]

Lemole

[11] Patent Number: 4,637,815

[45] Date of Patent: Jan. 20, 1987

[54] IRRIGATIONAL HEMOSTATIC SOLUTION

[76] Inventor: Gerald M. Lemole, 404 Tomlinson Rd., Huntingdon Valley, Pa. 19046

[21] Appl. No.: 763,056

[22] Filed: Aug. 6, 1985

[51] Int. Cl.$^4$ ............................................. A61M 31/00
[52] U.S. Cl. ....................................... 604/28; 604/49; 604/290; 424/94
[58] Field of Search ......................... 128/1 R; 424/94; 604/28, 48, 49, 290

[56] References Cited

U.S. PATENT DOCUMENTS 2,718,487  9/1955  Marx et al. .

OTHER PUBLICATIONS

Lambert et al., "The Treatment of Postoperative Bleeding Using E-Aminocaproic Acid, Cryoprecipitate, Fresh Frozen Plasma and Protamine Sulfate", Annals of Thoracic Surg., vol. 28, No. 5, Nov. 1979.

Primary Examiner—Dalton L. Truluck
Attorney, Agent, or Firm—Robert J. Mooney

[57] ABSTRACT

A method and solution for enhancing coagulation. The solution comprises a pharmacologically active mixture of calcium chloride, epsilon-aminocaproic acid, protamine, thrombin and norepinephrine dissolved in a saline solution. The solution is applied topically.

12 Claims, No Drawings

IRRIGATIONAL HEMOSTATIC SOLUTION

BACKGROUND OF THE INVENTION

Open heart surgery, while being performed on a daily basis across the country, is by its nature a most serious form of major surgery. Improved techniques and skills have increased the success of this operation and many patients benefit from the procedure.

One ever present problem which follows open heart surgery is post-operative bleeding. Post operative bleeding contributes to depletion of valuable blood products and significantly increases the physiologic strain experienced by the patient. But surgical bleeding is a local phenomenon, not systemic, and is best treated by local methods because systemic enhancement of the coagulation cascade can cause vein graft occlusion, valve thrombosis, phlebitis or drug toxicity. On the other hand, some coagulation enhancers cannot be given systemically or in sufficient quantities for the desired effect.

It has been observed that most patients who have undergone open heart surgery, and who are operated on again within a short time for one reason or another, exhibit no specific or localized sites of bleeding although they may have experienced significant blood loss. It is from this observation that the conclusion is reached that blood loss occurs over a relatively wide area and not localized sites, and is caused by fibrinolysis throughout the area and by the action of circulating fibrinolysins.

One compound, thrombin, has been proposed as a blood clotting preparation in U.S. Pat. No. 2,532,348, and in fact is presently an accepted treatment agent for clotting. U.S. Pat. No. 2,718,487 also teaches the effectiveness of thrombin, and proposes an improvement in which the thrombin is reacted with an acricline compound to form a reaction product. Of course the use of thrombin is not a universal cure, as disclosed in U.S. Pat. No. 4,364,861 and U.S. Pat. No. 4,391,746 where treatments specifically free of thrombin are prepared. The last two patents teach that the injection of thrombin into a human is considered highly dangerous.

The specific problem of excessive hemorrhage after cardiopulmonary bypass surgery is discussed in an article by Cary J. Lambert, MD, and others, entitled *The Treatment of Postperfusion Bleeding Using E-Aminocaproic Acid, Cryoprecipitate, Fresh-Frozen Plasma, and Protamine Sulfate*, published in the Annals of Thoracic Surgery, Vol. 28 No. 5, November 1979. In that article the problem of post operative bleeding is discussed. Several treatments are suggested. In the case of compensated hyperfibrinolysis (i.e., fibrinolysis without coagulation factor deficiencies) as measured by identified tests, epsilon-aminocaproic acid, AMICAR was intravenously administered. For uncompensated hyperfibrinolysis, cryoprecipitate and possibly plasma were also given. Where unneutralized heparin was detected in tests, protamine sulfate was given in an appropriate dose as determined by assay. In each case, close and rapid monitoring of the patient with rapid hematological assessment is needed.

This last mentioned cause of excessive hemorrhage, unneutralized heparin, is a problem which occurs because heparin is administered to stop the coagulation process during surgery. After surgery, treatment is needed to reverse circulating heparin and to prevent heparin rebound, which sometimes occurs with the reentry of heparin into the bloodstream from the patient's tissues. To prevent this, protamine sulfate is used to bind heparin, but this strong organic base has only been found to be effective on circulating heparin. Again, close monitoring of heparin levels is needed to provide a suitable treatment.

At present there is not a satisfactory treatment of post operative bleeding which is safe, fast, and is not dependant on time consuming laboratory tests.

SUMMARY OF THE INVENTION

It has now been discovered that control of post operative bleeding following open heart surgery can be achieved in the following manner.

Specifically, a method has been discovered for reducing mediastinal fibrinolysis in open heart surgery patients. The method comprises the steps of topically applying a hemostatic solution to the mediastinum, followed by closing the pericardium. The solution comprises a saline solution (commonly a 0.9% solution) at body temperature. Dissolved in the saline solution is a pharmacologically active mixture of Calcium Chloride, epsilon-aminocaproic acid, protamine, thrombin and norepinephrine.

The solution may be applied to the patient by bathing the pericardial sac and wound with the solution for a period of time, such as from 3 to 10 minutes, while slowly adding additional solution. The overflow is aspirated at the upper end of the incision. Next the sternum is closed and a quantity of solution is placed in the pericardium until the skin closure and dressing application are begun. At that time the pericardium and mediastinum are vacuum drained.

The solution preferrably contains from 0.5 to 5.0 grams of calcium chloride, 2 grams to 20 grams of epsilon-aminocaproic acid, 0.3 to 3.0 grams of protamine, 2500 units to 15,000 units of thrombin, and 0.05 milligrams to 4.0 milligrams of norepinephrine, with each quantity based upon one liter of saline solution. All are soluble therein.

A most preferred solution contains in one liter of saline solution about 1 gram of calcium chloride, 10 grams of epsilon-aminocaproic acid, 1 gram of protamine, 5000 units of thrombin, and 1 milligram of norepinephrine. The solution is preferrably formed by admixing the components with the saline solution followed by warming the solution to body temperature. The solution should then be used on a patient within four hours of preparation.

DESCRIPTION OF THE PREFERRED EMBODIMENT

As had been stated above, in most of the post operative open heart surgery patients who are returned to the operating room for various reasons for additional surgery, no definite site of bleeding was found. Nevertheless, 40% of the open heart patients will have circulating fibrinolysins. Moreover, heparin can and does accumulate in body tissues and is released into the bloodstream after circulatory protamine has been metabolized.

The solution employed herein comprises the recited ingredients dissolved in a saline solution such as warm Isotonic Ringers Solution, and is warmed to body temperature prior to application because it is a topical treatment.

The first ingredient, calcium chloride, is available from a wide number of pharmaceutical companies in sufficient purity and is freely soluable in both water and other solvents. The range of calcium chloride may be from 0.5 grams to 5.0 grams per liter.

Epsilon-aminocaproic acid is also known as AMICAR and is available under this name from Lederle Laboratories in pharmaceutically pure form. AMICAR is soluable in water and may be prepared as crystals in alcohol from epsilon-benzoylaminocapronitrile. Generally, from 2 to 20 grams per liter of saline solution will be used in the solution of this invention. As used herein, the term AMICAR is intended to mean any of the pharmaceutically equivalent or near equivalent forms of epsilon-aminocaproic acid.

Protamine is a term used for the group of simple proteins that yield basic amino acids on hydrolysis and they occur combined with nucleic acid. Protamines contain several kinds of amino acids, such as arginine, alanine, and serine. Most forms of protamine contain proline and valine, and may contain glycine and isoleucine. They are all soluble in water. Generally, from about 0.3 grams to 3.0 grams of protamine per liter of solution is used. Any pharmaceutical source of protamine may be used in this invention, and many such suppliers are available as this component is used systemically as an antidote for heparin, as previously discussed.

Thrombin is a serine proteinase present in blood plasma in the form of a precursor known as prothrombin. Thrombin plays a central part in the mechanism of blood coagulation, as has been discussed above. Various pharmaceutical sources of this component are available. Generally from 2,500 units to 15,000 units per liter of solution is a desirable level of addition.

The final component, norepinephrine, is generally added in an amount ranging from about 0.05 mg to 4.0 mg. Norepinephrine is generally known as 4-(2-Amino-1-hydroxyethyl)-1,2-benzenediol, and is freely soluble in water.

All of these components are added to a saline solution suitable for use with open heart surgery patients, such as Isotonic Ringers Solution for example. Some of the components are difficult to keep over extended periods, and the solution should be prepared no more than four hours before use. Thrombin, for example, needs to be refrigerated to keep, and protamine is actually unstable for any significant length of time except in the freeze dried form.

Once each of the ingredients are added to the saline solution, the admixture should be warmed to a temperature at or just slightly above body temperature. Normally about two liters of solution will be used in treating a patient. Properly applied, as will be apparent from a further reading of this description, the solution of this invention provides surprising and significant advantages. Recent experience has shown that there is an average of 48% blood loss decrease and a 38% blood usage decrease. Moreover, it is now for the first time substantially easier to predict a true bleeder, that is, one who has a surgically correctable problem.

EXAMPLES

In the following examples, solutions as disclosed above were used. For each liter of Isotonic Ringers Solution, 1 gram of calcium chloride, 10 grams of AMICAR, 1 gram of protamine, 5000 units of thrombin and 1 mg of norepinephrine were dissolved therein and the solution was warmed to body temperature for use within four hours of admixture. Efficacious results were also obtained by dissolving like amounts of the foregoing constituents in different volumes of Isotonic Ringers Solution ranging from 0.5 to 2.0 liters.

The procedure for using the solution to reduce mediastinal fibrinolysis is as follows. Upon termination of a bypass operation where protamine has been given internally to counteract the heparin, and after the cardiotomy suction has been turned off, the solution is applied. The pericardial sac and wound is bathed with the solution for a period of time adequate to substantially reduce the fibrinolysis. Normally, from 2 to 10 minutes is adequate, with about 5 minutes being the usual amount of time. During this time, new solution is slowly added while the overflow is aspirated at the upper end of the incision. After this time, the sternum is closed and an adequate quantity of solution is instilled in the pericardium and simply left there until the skin closure and dressing application begins. The quantity of solution may range from 100 cc or less to 300 cc or more, with about 200 cc of solution being typical.

Upon skin closure, the pericardium and mediastinum is sucked dry and the patient is attached to the chest drainage set-up in a standard manner. The topically applied treatment has thus been accomplished, with improved results noted. Most importantly, the patient's coagulation profile is not altered by this treatment, and depletion of valuable blood products and physiological strain is materially reduced.

A retrospective study of over 100 patients has shown a statistically significant difference in blood therapy. Illustrating the efficiency of this invention are several cases set forth below.

CASE ONE

A 49 year old Jehovah's Witness patient has an aortic valve replaced. Six months later, the patient had developed endocardites with renal failure and anemia. Specific values showed hemoglobin at 7.7, BUN 70 and Creatinine 7.0. During surgery the patient had extensive adhesions and a large paravalvular leak. Then the patient was dialyzed on bypass and the treatment of this invention was applied after bypass. The patient lost 220 cc of blood post operatively, but no blood was given. Though his hemoglobin dropped to 5.9, it returned to normal after two months.

CASE TWO

A 52 year old male had severe coronary artery disease. Upon completion of four bypasses, no protamine was given systemically. Instead a topically applied treatment according to the present invention was used to control local bleeding. The patient left the operating room with an activated clotting time (ACT) of 500 seconds, which is 5 times normal.

CASE THREE

A 60 year old male was given an aortic valve replacement in an operation in which the present irrigational solution was not used. The patient had persistent bleeding which caused the surgeon to re-operate on the patient three times during the night. The last re-operation was performed by a senior surgeon to make sure that nothing was overlooked. The hemorrhage persisted. In desperation, the surgeon introduced the irrigational solution of this invention topically through the chest tube for about 10 minutes. The bleeding stopped and the patient made an uneventful recovery.

OTHER RESULTS

To assess the efficiency of this invention, the aforementioned retrospective review was made to compare 37 parameters in 50 control patients who were not treated in accordance with this invention and 52 patients treated as described herein. Pre and post operative laboratory profiles as well as mediastinal drainage and blood product use through time were examined. All patients had similar pre and post operative laboratory profiles, cross-clamp bypass time, hospital stay and complication rates. In the first two hours, an overall decrease of 45% in mediastinal drainage was documented, and a 32% decrease in 48 hours. This was equal to about 450 cc per patient per 48 hours. While PRBC and albumin transfusions were similar as is expected, fresh frozen plasma use in the treated patients decreased by 29%. In high risk patient groups, such as over 45 years of age or with a bypass time longer than 60 minutes, bleeding decreased 38% in the former and 41% in the latter. Patients with valvular surgery had an overall decrease of 41%, compared to untreated patients.

OTHER BENEFITS

Initially the question of the possibility of post operative adhesions from the use of the solution was considered. Laboratory studies with guinea pigs showed no inflammatory changes of several surfaces where the solution was left in the peritonium for six weeks. One patient required unrelated operative work which permitted examination two months after surgery using this procedure. Both pericardial and epicardial surfaces were free of adhesions. It is now expected that use of the present invention should aid in the prevention of adhesions because most of the blood, which is the prime cause of dense adhesions, is removed by this method.

It has been found through the evaluation of this invention that the average patient bleeds from 50 cc to 100 cc in the first hour after surgery. By taking serial samples of the chest drainage, it has been shown that the hematocrit of the drainage is between 3% and 12%. This is due to some solution dilution of the pericardial fluid. However, if the hematocrit of drainage is over 25% and if chest drainage is over 250 cc in the first hour after surgery, the likelihood of surgical intervention to correct bleeding is very high. Therefore, it is possible to determine criteria which would allow a surgeon to more accurately and more quickly identify the need for intervention. Blood use, delay and emergency surgery would decrease.

As used throughout a unit of thrombin means a U.S. (NIH) unit of thrombin defined as the amount of thrombin required to clot one milliliter of standardized fibrinogen solution in fifteen (15) seconds.

Other advantages and uses of the present invention will become apparent to one skilled in the art upon reading this disclosure.

Having thus described the invention, what is claimed is:

1. A method of reducing mediastinal fibrinolysis in open heart surgery patients, comprising the steps of:
topically applying a hemostatic solution to the mediastinum followed by closing the pericardium, said solution comprising a saline solution at body temperature of a pharmacologically active mixture of calcium chloride, epsilon-aminocaproic acid, protamine, thrombin and norepinephrine dissolved therein.

2. The method of claim 1 wherein said solution comprises from 0.5 to 5.0 grams of calcium chloride, 2 grams to 20 grams of epsilon-aminocaproic acid, 0.3 to 3.0 grams of protamine, 2,500 units to 15,000 units of thrombin and 0.05 mgm to 4.0 mgm of norepinephrine, each of said quantities based upon one liter of saline solution.

3. The method of claim 2 wherein said quantities comprises about 1 gram of calcium chloride, 10 grams of epsilon-aminocaproic acid, 1 gram of protamine, 5000 units of thrombin and 1 mg of norepinephrine, each in said 1 liter.

4. A method of reducing mediastinal fibrinolysis in open heart surgery patients, comprising the steps of:
topically applying a hemostatic solution by bathing the pericardial sac and wound with said solution for a pharmacalogically adequate time while slowly adding additional solution while aspirating the overflow, followed by installation in the pericardium of a quantity of solution after closure of the sternum and until the skin closure and dressing application are begun, at which time the pericardium and mediastinum is drained, said solution comprising a saline solution at body temperature of a pharmacologically active mixture of calcium chloride, epsilon-aminocaproic acid, protamine, thrombin and norepinephrine dissolved therein.

5. The method of claim 4 wherein said time is from 3 to 10 minutes.

6. The method of claim 5 where said time is about 5 minutes and said quantity is from 100 to 300 cc.

7. The method of claim 6 where said quantity is about 200 cc.

8. The method of claim 4 wherein said solution comprises from 0.5 to 5.0 grams of calcium chloride, 2 grams to 20 grams of epsilon-aminocaproic acid, 0.3 to 3.0 grams of protamine, 2500 units to 15000 units of thrombin and 0.05 mgm to 4.0 mgm of norepinephrine, each of said quantities based upon liter of saline solution.

9. The method of claim 8 where said quantities comprises about 1 gram of calcium chloride, 10 grams of Amicar, 1 gram of protamine, 5000 units of thrombin and 1 mg of norepinephrine, each in said liter.

10. A solution comprising:
a saline solution of pharmacologically active mixture of calcium chloride, epsilon-aminocaproic acid, protamine, thrombin and norepinephrine dissolved therein.

11. The solution of claim 10 where said solution comprises from 0.5 to 5.0 grams of calcium chloride, 2 grams to 20 grams of epsilon-aminocaproic acid, 0.3 to 3.0 grams of protamine, 2500 units to 15000 units of thrombin and 0.05 mgm to 4.0 mgm of norepinephrine, each of said quantities based upon one liter of saline solution.

12. The solution of claim 11 where said quantities comprise about 1 gram of calcium chloride, 10 grams of epsilon-aminocaproic acid, 1 gram of protamine, 5000 units of thrombin and 1 mg of norepinephrine, each in said liter.

* * * * *